United States Patent [19]

Waters

[11] Patent Number: 5,621,667
[45] Date of Patent: Apr. 15, 1997

[54] LIFT TASK ANALYSIS SYSTEM

[75] Inventor: Thomas R. Waters, Fairfield, Ohio

[73] Assignee: The United States of America as represented by the Department of Health and Human Services, Washington, D.C.

[21] Appl. No.: 590,060

[22] Filed: Jan. 17, 1996

Related U.S. Application Data

[63] Continuation of Ser. No. 159,284, Nov. 30, 1993, abandoned.

[51] Int. Cl.$^6$ ................................................ G01G 19/44
[52] U.S. Cl. .................... 364/567; 364/550; 364/413.01; 128/781; 128/782
[58] Field of Search ........................ 364/567, 505, 364/550, 463, 413.01, 413.02, 506; 414/560, 561, 693–695; 128/781, 782; 73/865.1, 865.03, 865.04, 379.01–379.03, 379.05, 379.06, 379.08; 482/5.8, 112, 93, 96; 273/440, 451

[56] References Cited

U.S. PATENT DOCUMENTS

| | | | |
|---|---|---|---|
| 4,723,557 | 2/1988 | Gross | 128/781 |
| 4,768,779 | 9/1988 | Oehman, Jr. et al. | 482/5 |
| 4,882,677 | 11/1989 | Curran | 364/413.02 |
| 4,890,495 | 1/1990 | Slane | 73/379.06 |
| 4,912,638 | 3/1990 | Pratt, Jr. | 364/413.02 |
| 4,972,711 | 11/1990 | Jain et al. | 73/379.06 |
| 5,143,088 | 9/1992 | Marras et al. | 128/781 |
| 5,151,071 | 9/1992 | Jain et al. | 482/5 |
| 5,178,160 | 1/1993 | Gracovetsky et al. | 482/112 |
| 5,275,045 | 1/1994 | Johnston et al. | 73/379.01 |
| 5,361,775 | 11/1994 | Remesetal | 128/781 |
| 5,442,729 | 8/1995 | Kramer et al. | 128/782 |

OTHER PUBLICATIONS

Stansfield, Experiments in Robotic Sensorimotor Control During Grasp, IEEE Transaction Systems, Manand Cybernetics, vol. 23, No. 3 May/Jun. 1993 pp. 891–896.
Revised NIOSH Equation for the Design and Evaluation of Manual Lifting Tasks, by Thomas R. Waters, et al., Ergonomics.
"Back Injury at Work: A New Beginning for Prevention", Ergonomics, vol. 36, No. 7 (1993), pp. 747–748.
Applications Manual for the Revised NIOSH Lifting Equation, by Thomas R. Waters, et al. (May 20, 1993), Appendix I.
Revised NIOSH Equation for the Design and Evaluation of Manual Lifting Tasks, by Thomas R. Waters, et al., vol. 36, No. 7 (1993), pp. 749–776, Appendix II.

(List continued on next page.)

*Primary Examiner*—Edward R. Cosimano
*Assistant Examiner*—Hal D. Wachsman
*Attorney, Agent, or Firm*—Lowe, Price, LeBlanc & Becker

[57] ABSTRACT

A lift task analysis system includes a sensor having a retractable cable grasped by the hands of a participant. The participant moves in accordance with a selected lifting task and, in doing so, move the cable end correspondingly. The sensor generates an output indicative of a location of the mid-point of the participant's hands holding the cable end with respect to that sensor, i.e., a position of the end of the extended cable. The sensor is attached to the housing of an analysis device which includes an input for receiving user/selected parameters. The housing also includes a control processor with means for determining a recommended weight limit and means for determining a lifting index. These determinations are made based upon user-selected input and NIOSH equation multipliers automatically determined through the use of the sensor. The system also includes a memory for storing the lifting index and the recommended weight limit for a plurality of different lifting tasks, as well as other data relevant to those lifting tasks.

20 Claims, 8 Drawing Sheets

OTHER PUBLICATIONS

Revisions in NIOSH Guide to Manual Lifting, by V. Putz-Anderson et al., Apr. 9, 1991, Appendix III.

Scientific Support Document for the Revised 1991 NIOSH Lifting Equation: Technical Contract Reports, May 8, 1991, Appendix IV.

Proceedings of the Human Factors and Ergonomics Society, 37th Annual Meeting, Oct. 11–15, 1993, Seattle, Washington. "Designing for Diversity"; vol. 2.

McGlothlin et al., "Occupational Back Injuries—Controlling the Epidemic", Proceedings of the 7th Annual Conference of the IEEE/Engineering in Medicine and Biology Society, vol. 1, Chicago, Illinois, Sep. 27–30, 1995.

R.G. Hazard et al., "Test–retest Variation in Lifting Capacity and Indices of Subject Effort", Clinical Biomechanics, vol. 8, No. 1, Jan. 1993.

HORIZONTAL MULTIPLIER AT THE DESTINATION ($HM_d$) IS
COMPUTED AS FOLLOWS:
$HM_d$ = 10/Hd IN INCHES

VERTICAL MULTIPLIER AT THE DESTINATION ($VM_d$) IS
COMPUTED AS FOLLOWS:
$VM_d$ = 1 -(.0075 x ABS($V_d$- 30))

DISTANCE MULTIPLIER AT THE DESTINATION ($DM_d$) IS
COMPUTED AS FOLLOWS:
$DM_d$ = .82 + (1.8/$D_d$)

ASYMMETRIC MULTIPLIER AT THE DESTINATION ($AM_d$) IS
COMPUTED AS FOLLOWS:
$AM_d$ = 1 -(.0032 x $A_d$)

FIG. 4A

LIFT TASK ANALYSIS SYSTEM

This application is a continuation of application Ser. No. 08/159,284 filed Nov. 30, 1993 now abandoned.

TECHNICAL FIELD

This invention relates to a lift task analysis apparatus using the National Institute for Occupational Safety and Health (NIOSH) equations to determine the position of the mid-point of a person's hands at the start and end of a specified lift in a fixed three-dimensional frame of reference coordinates for a particular lifting task. More particularly, the present invention relates to apparatus for taking measurements, automatically determining physical parameters and NIOSH equation multipliers, and calculating the results of the NIOSH equations based upon those measurements.

BACKGROUND ART

Low back pain and injuries attributed to manual lifting activities continue as one of the leading occupational health and safety issues facing preventive medicine. Despite efforts at control, including programs directed at both workers and jobs, work-related back injuries still account for a significant proportion of human suffering and economic cost to this nation. The scope of the problem was summarized in a report entitled *Back Injuries*, prepared by the Department of Labor's Bureau of Labor Statistics [DOL(BLS)], Bulletin, published in 1982.

The DOL's conclusions are consistent with current workers' compensation data indicating that "injuries to the back are one of the more common and costly types of work-related injuries." According to the DOL report, back injuries accounted for nearly 20% of all injuries and illnesses in the workplace, and nearly 25% of the annual worker's compensation payments. A more recent report by the National Safety Council (*Accident Facts,* 1990) indicated that overexertion was the most common cause of occupational injury, accounting for 31% of all injuries. The back, moreover, was the body part most frequently injured (22% of 1.7 million injuries) and the most costly to workers' compensation systems.

More than ten years ago, the National Institute for Occupational Safety and Health (NIOSH) recognized the growing problem of work-related back injuries and published the *Work Practices Guide for Manual Lifting* (WPG) (DHHS(NIOSH), 1981). The WPG (1981) contained a summary of the lifting-related literature before 1981; analytical procedures and a lifting equation for calculating a recommended weight for specified two-handed, symmetrical lifting tasks; and an approach for controlling the hazards of low back injury from manual lifting. The approach to hazard control was coupled to the Action Limit (AL), a resultant term that denoted the recommended weight derived from the lifting equation.

In 1985, the National Institute for Occupational Safety and Health (NIOSH) convened an ad hoc committee of experts who reviewed the current literature on lifting, including the 1981 NIOSH WPG. The literature review was summarized in a document entitled "Scientific Support Documentation for the Revised 1991 NIOSH Lifting Equation: Technical Contract Reports, May 8, 1991," which is available from the National Technical Information Service (NTIS No. PB-91-226-274). The literature summary contains updated information on the physiological, biomechanical, psychophysical, and epidemiological aspects of manual lifting. Based on the results of the literature review, the ad hoc committee recommended criteria for defining the lifting capacity of healthy workers. The committee used the criteria to formulate a revised lifting equation (as indicated on page 4 of this application). The equation was publicly presented in 1991 by NIOSH staff at a national conference in Ann Arbor, Mich. entitled: "A National Strategy for Occupational Musculoskeletal Injury Prevention—Implementation Issues and Research Needs." Subsequently, NIOSH staff developed the documentation for the equation and played a prominent role in recommending methods for interpreting the results of the lifting equation. The revised lifting equation reflects new findings and provides methods for evaluating asymmetrical lifting tasks, and lifts of objects with less than optimal couplings between the object and the worker's hands. The revised lifting equation also provides guidelines for a larger range of work durations and lifting frequencies than the earlier equation (WPG, 1981).

The rationale and criterion for the development of the revised NIOSH lifting equation are provided in a separate journal article entitled: "Revised NIOSH Equation for the Design and Evaluation of Manual Lifting Tasks," by Waters, Putz-Anderson, Garg, and Fine, 1993. This article provides an explanation of the selection of the biomechanical, physiological, and psychophysical criterion, as well as a description of the derivation of the individual components of the revised lifting equation.

Although the revised lifting equation has not been fully validated, the recommended weight limits derived from the revised equation are consistent with, or lower than, those generally reported in the literature, and are more likely to protect healthy workers for a wider variety of lifting tasks than methods that rely only a single task factor or single criterion.

Definitions, restrictions/limitations and data requirements for the revised lifting equation are provided below.

The RWL is the principal product of the revised NIOSH lifting equation. The RWL is defined for a specific set of task conditions as the weight of the load that nearly all healthy workers could perform over a substantial period of time (e.g., up to 8 hours) without an increased risk of developing lifting-related LBP.

$$RWL = LC \times HM \times VM \times DM \times AM \times FM \times CM$$

NIOSH also developed a secondary term, the Lifting Index providing a relative estimate of the level of physical stress associated with a particular manual lifting task. The estimate of the level of physical stress is defined by the relationship of the weight of the load lifted (L) and the recommended weight (RWL). The LI is defined by the following equation:

$$LI = \frac{LoadWeight}{RecommendedWeightLimit} = \frac{L}{RWL}$$

The lifting equation is a tool for assessing the physical stress of two-handed manual lifting tasks. As with any tool, its application is limited to those conditions for which it was designed. Specifically, the lifting equation was designed to meet specific lifting-related criteria that encompass biomechanical, work physiology, and psychophysical assumptions and data, identified above. To the extent that a given lifting task accurately reflects these underlying conditions and criteria, this lifting equation may be appropriately applied.

The 1991 lifting equation does not include task factors to account for unpredicted conditions, such as unexpectedly heavy loads, slips, or falls. Additional biomechanical analyses may be required to assess the physical stress on joints that occur from traumatic incidents. Moreover, if the environment is unfavorable (e.g., temperatures or humidity significantly outside the range of 19° to 26° C. [66° to 79° F.] or 35% to 50%, respectively) independent metabolic assessments would be needed to gauge the effects of these variables on heart rate and energy consumption.

The 1991 lifting equation is limited in that it was not designed to assess tasks involving one-handed lifting, lifting while seated or kneeling, or lifting in a constrained or restricted work space. The equation also does not apply to lifting unstable loads, lifting of wheel barrows, shoveling, or high-speed lifting. For such task conditions, independent and task specific biomechanical, metabolic, and psychophysical assessments may be needed.

The use of the 1991 lifting equation requires the assumption that the worker/floor surface coupling provides at least a 0.4 (preferably 0.5) coefficient of static friction between the shoe sole and the working surface. An adequate worker/floor surface coupling is necessary when lifting to provide a firm footing and to control accidents and injuries resulting from foot slippage. A 0.4 to 0.5 coefficient of static friction is comparable to the friction found between a smooth, dry floor and the sole of a clean, dry leather work shoe (nonslip type). Independent biomechanical modeling may be used to account for variations in the coefficient of friction.

The use of the 1991 lifting equation requires the additional assumption that lifting and lowering tasks have the same level of risk for low back injuries (i.e. that lifting a box from the floor to a table is as hazardous as lowering the same box from a table to the floor). This assumption may not be true if the worker actually drops the box rather than lowering it all the way to the destination. Independent metabolic and/or psychophysical assessments may be needed to assess worker capacity for various lowering conditions.

The following list of brief definitions are useful in applying the revised NIOSH lifting equation. For detailed descriptions of these terms, refer to the individual sections where each is discussed. Exemplary methods for measuring these variables and examples may be found in "Applications Manual for the Revised NIOSH Lifting Equation", by Thomas R. Waters et al, May 20, 1993.

Lifting task is defined as the act of manually grasping an object of definable size and mass with two hands, and vertically moving the object without mechanical assistance.

Load Weight (L) is the weight of the object to be lifted, in pounds, including the container.

Horizontal location (H) is the distance of the hands away from the mid-point between the ankles, in inches (measure at the origin and destination of lift). See FIG. 6.

Vertical location (V) is the distance of the hands above the floor, in inches (measure at the origin and destination of lift). See FIG. 6.

Vertical travel distance (D) is the absolute value of the difference between the vertical heights at the destination and origin of the lift, in inches.

Angle of asymmetry (A) is the angular measure of how far the object is displaced from the front (mid-sagittal plane) of the worker's body at the beginning or ending of the lift, in degrees (measure at the origin and destination of lift). See FIG. 7.

Frequency of lifting (F) is the average number of lifts per minute over a 15 minute period.

Duration of lifting is the three-tiered classification of lifting duration specified by the distribution of work-time and recovery-time (work pattern). Duration is classified as either 1, 2, or 8 hours, depending on the work pattern.

Coupling classification is the classification of the quality of the hand-to-container coupling (e.g., handle., cut-out, or grip). Coupling quality is classified as good, fair, or poor.

Significant Control is defined as a condition requiring "precision placement" of the load at a destination of the lift. This is usually the case when (1) the worker has to re-grasp the load near the destination of the lift, (2) the worker has to momentarily hold the object at the destination, or (3) the worker has to position or guide the load at the destination.

The revised lifting equation for calculating the Recommended Weight Limit (RWL), as previously set out on page 4) is based on a multiplicative model that provides a weighting for each of six task variables. The weightings are expressed as coefficients that serve to decrease the load constant, which represents the maximum recommended load weight to be lifted under ideal conditions.

$$RWL = LC \times HM \times VM \times DM \times AM \times FM \times CM$$

Where:

LC=Load Constant=51 lb

HM=Horizontal Multiplier=(10/H)

VM=Vertical Multiplier=$1-(0.0075|V-30|)$

DM=Distance Multiplier=0.82+(1.8/D)

AM=Asymmetric Multiplier=1-(0.0032 A)

FM=Frequency Multiplier=From Table 1

CM=Coupling Multiplier=From Table 2

The term "task variables" refers to the measurable task descriptors (i.e., H, V, D, A, F, and C); whereas, the term "multipliers" refers to the reduction coefficients in the equation (i.e., HM, VM, DM, AM, FM, and CM).

Each multiplier should be computed from the appropriate formula, but in some cases it will be necessary to use linear interpolation to determine the value of a multiplier, especially when the value of a variable is not directly available from a table. For example, when the measured frequency is not a whole number, the appropriate multiplier must be interpolated between the frequency values in the table for the two values that are closest to the actual frequency. Following is a brief discussion of the task variables, the restrictions, and the associated multiplier for each component of the model.

Horizontal location (H) is measured from the midpoint of the line joining the inner ankle bones to a point projected on the floor directly below the mid-point of the hand grasps (i.e., load center), as defined by the large middle knuckle of the hand (FIG. 6). If significant control is required at the destination (i.e., precision placement), then H should be measured at both the origin and destination of the lift.

In those situations where the H value can not be measured, then H may be approximated from the following equations:

$$H = 8 + W/2 \text{ for } V \geq 10 \text{ inches}$$

$$H = 10 + W/2 \text{ for } V < 10 \text{ inches}$$

Where: W is the width of the container in the sagittal plane and V is the vertical location of the hands from the floor.

If the horizontal distance is less than 10 inches, then H is set to 10 inches. Although objects can be carried or held closer than 10 inches from the ankles, most objects that are closer than this cannot be lifted without encountering interference from the abdomen or hyperextending the shoulders. While 25 inches was chosen as the maximum value for H, it is probably too large for shorter workers, particularly when lifting asymmetrically. Furthermore, objects at a distance of more than 25 inches from the ankles normally cannot be lifted vertically without some loss of balance.

The Horizontal Multiplier (HM) is 10/H, for H measured in inches, and HM is 25/H, for H measured in centimeters.

If H is less than or equal to 10 inches, the multiplier is 1.0. HM decreases with an increase in H value. The multiplier for H is reduced to 0.4 when H is 25 inches. If H is greater than 25 inches, then HM=0.

Vertical location (V) is defined as the vertical height of the hands above the floor. V is measured vertically from the floor to the mid-point between the hand grasps, as defined by the large middle knuckle. The coordinate system is illustrated in FIG. 6.

The vertical location (V) is limited by the floor surface and the upper limit of vertical reach for lifting (i.e., 70 inches). The vertical location should be measured at the origin and the destination of the lift to determine the travel distance (D).

To determine the Vertical Multiplier (VM), the absolute value or deviation of V from an optimum height of 30 inches is calculated. A height of 30 inches above floor level is considered "knuckle height" for a worker of average height (66 inches). The Vertical Multiplier (VM) is $(1-(0.0075|V-30|))$ for V measured in inches.

When V is at 30 inches, the vertical multiplier (VM) is 1.0. The value of VM decreases linearly with an increase or decrease in height from this position. At floor level, VM is 0.78, and at 70 inches height VM is 0.7. If V is greater than 70 inches, then VM=0.

The Distance variable (D) is defined as the vertical travel distance of the hands between the origin and destination of the lift. For lifting, D can be computed by subtracting the vertical location (V) at the origin of the lift from the corresponding V at the destination of the lift (i.e., D is equal to V at the destination minus V at the origin). For a lowering task, D is equal to V at the origin minus V at the destination.

The Distance variable (D) is assumed to be at least 10 inches, and no greater than (70-V) inches. If the vertical travel distance is less than 10 inches, then D should be set to the minimum distance of 10 inches.

The Distance Multiplier (DM) is $(0.82+(1.8D))$ for D measured in inches. For D less than 10 inches D is assumed to be 10 inches, and DM is 1.0. The Distance Multiplier, therefore, decreases gradually with an increase in travel distance. The DM is 1.0 when D is set at 10 inches; DM is 0.85 when D=70 inches. Thus, DM ranges from 1.0 to 0.85 as the D varies from 0 inches to 70 inches.

Regarding the asymmetry component, asymmetry refers to a lift that begins or ends outside the sagittal plane. In general, asymmetric lifting should be avoided. If asymmetric lifting cannot be avoided, however, the recommended weight limits are significantly less than those limits used for symmetrical lifting.

An asymmetric lift may be required under the following task or workplace conditions:

1. The origin and destination of the lift are oriented at an angle to each other.
2. There is inadequate room to use a step turn.
3. The lifting motion is across the body, such as occurs in swinging bags or boxes from one location to another.
4. The lifting is done to maintain body balance in obstructed workplaces, on rough terrain, or on littered floors.
5. Productivity standards require reduced time per lift.

The asymmetric angle (A), which is depicted graphically in FIG. 6, is operationally defined as the angle between the asymmetry line and the sagittal line. The asymmetry line is defined as the line that joins the mid-point between the inner ankle bones and the point projected on the floor directly below the mid-point of the hand grasps, as defined by the large middle knuckle. The sagittal line is defined as the line passing through the mid-point between the inner ankle bones and lying in the sagittal plane, as defined by the neutral body position (i.e., hands directly in front of the body, with no twisting at the legs, torso, or shoulders).

The asymmetry angle (A) must always be measured at the origin of the lift. If significant control is required at the destination, however, then angle A should be measured at both the origin and the destination of the lift. The angle A is limited to the range from 0° to 135°. If A>135°, then AM is set equal to zero, which results in a RWL of zero, or no load.

The Asymmetric Multiplier (AM) is $1-(0.0032A)$. The AM has a maximum value of 1.0 when the load is lifted directly in front of the body. The AM decreases linearly as the angle of asymmetry (A) increases. The range is from a value of 0.57 at 135° of asymmetry to a value of 1.0 at 0° of asymmetry (i.e., symmetric lift). If A is greater than 135°, then AM=0, and the load is zero.

The frequency multiplier is defined by (a) the number of lifts per minute (frequency), (b) the amount of time engaged in the lifting activity (duration), and (c) the vertical height of the lift from the floor. Lifting frequency (F) refers to the average number of lifts made per minute, as measured over a 15-minute period. Because of the potential variation in work patterns, analysts may have difficulty obtaining an accurate or representative 15-minute work sample for computing the lifting frequency (F). If significant variation exists in the frequency of lifting over the course of the day, analysts should employ standard work sampling techniques to obtain a representative work sample for determining the number of lifts per minute. For those jobs where the frequency varies from session to session, each session should be analyzed separately. In any event, the overall work pattern must still be considered. For more information, most standard industrial engineering or ergonomics texts provide guidance for establishing a representative job sampling strategy (e.g., Eastman Kodak Company, 1986).

For tasks with lifting frequencies below 0.2 lifts per minute (1 lift every five minutes), the lifting frequency is set equal to 0.2 lifts per minute.

Lifting duration is classified into three categories based on the pattern of continuous work-time and recovery-time (i.e., light work) periods. A continuous work-time period is defined as a period of uninterrupted work. Recover-time is defined as the duration of light work activity following a period of continuous lifting. Examples of light work include activities such as sitting at a desk or table, monitoring operations, light assembly work, etc. The three categories are short-duration, moderate-duration and long-duration.

Lifting frequency (F) for repetitive lifting may range from 0.2 lifts/min to a maximum frequency that is dependent on the vertical location of the object (V) and the duration of lifting see Table 1 below.

TABLE 1

FREQUENCY MULTIPLIER TABLE

| | DURATION | | | | | |
|---|---|---|---|---|---|---|
| F | <1 hour | | 1–2 hours | | 2–8 hours | |
| lifts/min | V < 30 in | V ≧ 30 in | V < 30 in | V ≧ 30 in | V < 30 in | V ≧ 30 in |
| ≦2 | 1.00 | 1.00 | .95 | .95 | .85 | .85 |
| 5 | .97 | .97 | .92 | .92 | .81 | .81 |
| 1 | .94 | .94 | .88 | .88 | .75 | .75 |
| 2 | .91 | .91 | .84 | .84 | .65 | .65 |
| 3 | .88 | .88 | .79 | .79 | .55 | .55 |
| 4 | .84 | .84 | .72 | .72 | .45 | .45 |
| 5 | .80 | .80 | .60 | .60 | .35 | .35 |
| 6 | .75 | .75 | .50 | .50 | .27 | .27 |
| 7 | .75 | .70 | .42 | .42 | .22 | .22 |
| 8 | .60 | .60 | .35 | .35 | .18 | .18 |
| 9 | .52 | .52 | .30 | .30 | .00 | .15 |

TABLE 1-continued

FREQUENCY MULTIPLIER TABLE

| F | DURATION | | | | | |
|---|---|---|---|---|---|---|
| | <1 hour | | 1–2 hours | | 2–8 hours | |
| lifts/ min | V < 30 in | V ≧ 30 in | V < 30 in | V ≧ 30 in | V < 30 in | V ≧ 30 in |
| 10 | .45 | .45 | .26 | .26 | .00 | .13 |
| 11 | .41 | .41 | .00 | .23 | .00 | .00 |
| 12 | .37 | .37 | .00 | .21 | .00 | .00 |
| 13 | .00 | .34 | .00 | .00 | .00 | .00 |
| 14 | .00 | .31 | .00 | .00 | .00 | .00 |
| 15 | .00 | .28 | .00 | .00 | .00 | .00 |
| >15 | .00 | .00 | .00 | .00 | .00 | .00 |

Lifting above the maximum frequency results in a RWL of 0.0. (Except for the special case of discontinuous lifting discussed above, where the maximum frequency is 15 lifts/minute.)

The FM value depends upon the average number of lifts/min (F), the vertical location (V) of the hands at the origin, and the duration of continuous lifting. For lifting tasks with a frequency less than 0.2 lifts per minute, set the frequency equal to 0.2 lifts per minute. The FM is determined from Table 1.

Regarding the coupling component, the nature of the hand-to-object coupling or gripping method can affect not only the maximum force a worker can or must exert on the object, but also the vertical location of the hands during the lift. A "good" coupling will reduce the maximum grasp forces required and increase the acceptable weight for lifting, while a "poor" coupling will generally require higher maximum grasp forces and decrease the acceptable weight for lifting.

The effectiveness of the coupling is not static, but may vary with the distance of the object from the ground, so that a good coupling could become a poor coupling during a single lift. The entire range of the lift should be considered when classifying hand-to-object couplings, with classification based on overall effectiveness. The analyst must classify the coupling as good, fair, or poor. If there is any doubt about classifying a particular coupling design, then the more stressful classification should be selected.

Based on the coupling classification and vertical location of the lift, a "Good" coupling type has a Coupling Multiplier (CM) of 1.00 (regardless of the vertical location of the object (V)); a "Fair" coupling type has a coupling multiplier of 0.95 (when V<30 inches) or a coupling multiplier of 1.0 (when V≧30 inches); and a "Poor" coupling type has a coupling multiplier of 0.90 (regardless of the vertical location of the object (V)). The CM is determined from Table 2 below.

TABLE 2

COUPLING MULTIPLIER TABLE

| Coupling Type | CM | |
|---|---|---|
| | V < 30 in | V ≧ 30 in |
| GOOD | 1.00 | 1.00 |
| FAIR | .95 | 1.00 |
| POOR | .90 | .90 |

As defined earlier, the Lifting Index (LI) provides a relative estimate of the physical stress associated with a manual lifting job.

$$LI = \frac{LoadWeight}{RecommendedWeightLimit} = \frac{L}{RWL}$$

Where Load Weight (L)=weight of the object lifted (lbs.)

The recommended weight limit (RWL) and lifting index (LI) can be used to guide ergonomic design in several ways:

(1) The individual multipliers can be used to identify specific job-related problems. The relative magnitude of each multiplier indicates the relative contribution of each task factor (e.g., horizontal, vertical, frequency, etc.)

(2) The RWL can be used to guide the redesign of existing manual lifting jobs or to design new manual lifting jobs. For example, if the task variables are fixed, then the maximum weight of the load could be selected so as not to exceed the RWL; if the weight is fixed, then the task variables could be optimized so as not to exceed the RWL.

(3) The LI can be used to estimate the relative magnitude of physical stress for a task or job. The greater the LI, the smaller the fraction of workers capable of safely sustaining the level of activity. Thus, two or more job designs could be compared.

(4) The LI can be used to prioritize ergonomic redesign. For example, a series of suspected hazardous jobs could be rank ordered according to the LI and a control strategy could be developed according to the rank ordering (i.e., jobs with lifting indices above 1.0 or higher would benefit the most from redesign).

The NIOSH Recommended Weight Limit (RWL) equation and Lifting Index (LI) are based on the concept that the risk of lifting-related low back pain increases as the demands of the lifting task increase. In other words, as the magnitude of the lifting index increases, a greater percentage of the workforce is likely to be at risk for developing lifting-related low back pain. The exact shape of the risk function, however, is not known. Thus it is not possible to quantify the precise degree of risk associated with increments in the lifting index. From the NIOSH perspective, however, it is likely that lifting tasks with a LI≧1.0 pose an increased risk for lifting-related low back pain for some fraction of the workforce (Waters et al., 1993). Therefore, based on this judgment, the lifting index may be used to identify potentially hazardous lifting jobs or to compare the relative severity of two jobs for the purpose of evaluating and redesigning them.

Waters et al, supra, contains additional examples of the application of the NIOSH equations to various lifting tasks. In each one of these examples, it is necessary to calculate multipliers to be used in the equations from measurements taken, or to take readings from existing tables to provide the necessary multipliers. This is a tedious, time consuming process requiring the layout of multiple equations to determine such parameters as vertical displacement as well as the equation multipliers (HM, VM, DM, AM) before the results of the final two equations can be calculated. This measurement process is also susceptible to user error resulting in misleading data that is often dangerous to individuals carrying out the lifting task. Consequently, there is a tendency on the part of users to ignore the use of the NIOSH equations, if a lifting task has to be done quickly, or if the task does not seem to be worth the bother of going through the extensive calculations.

DISCLOSURE OF THE INVENTION

One object of the present invention is to provide a self-contained system in which the NIOSH equations can be applied quickly and with little chance of error.

Another object of the present invention is to provide a system in which a single physical measurement will suffice to provide spatial data for calculating all of the NIOSH equation multipliers.

Yet another object of the present invention is to provide apparatus for generating a data base including a plurality of lift task analyses to be contained in the same device used for making the physical measurements and carrying out the NIOSH equation calculations.

A further object of the present invention is to provide apparatus for automatically determining NIOSH equation multipliers indicative of physical parameters related to a lifting task under analysis.

It is still another object of the present invention to provide a system in which the user can input relevant data for use with the NIOSH equations in determining the overall analysis of a lifting task.

These and other objectives are carried out by a lift task analysis system including means for determining physical locations of the distal end and generating outputs in terms of three spherical polar coordinates relative to the origin, a horizontal plane containing the origin and a vertical plane containing the origin, a input means for enabling a user to input selected parameters, and a control processor. The control processor includes means for determining for a selected lifting task a recommended weight limit (according to the NIOSH equation) based upon the output of the sensor and user selected parameters. The control processor also includes means for determining for the selected lifting task a lifting index (according to the NIOSH equation) based upon the recommended weight limit and user-inputted parameters. Other aspects of the system further include a memory, a means for storing the results of the NIOSH equations, as well as other user input data appropriate for lift task analysis.

BRIEF DESCRIPTION OF THE DRAWINGS

FIG. 4A is a flow chart illustrating the necessary computations to determine four of the six NIOSH equation multipliers for the destination of the lift.

BEST MODE FOR CARRYING OUT THE INVENTION

Figure 1:
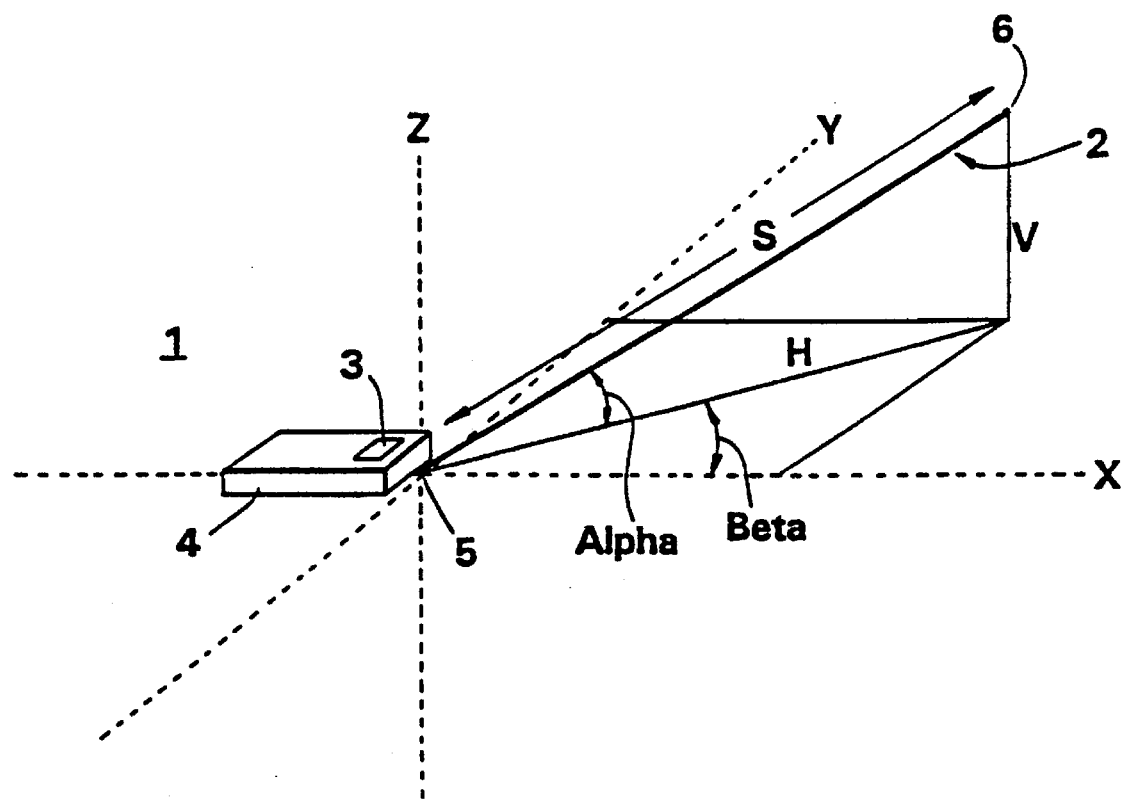
FIG. 1 is a diagram illustrating details of a polar coordinate system employed in use of the subject lift task analyzer to obtain position-related variables to be used in calculating various multipliers, recommended weight limits and lifting indexes.

A solution to the problems associated with using the NIOSH equations is found through the use of the system illustrated in FIG. 1. This system is contained in housing 4 which has accommodations for a display 3 and a user input device such as a keyboard (not shown). It is noted that the user input device can consist of any of a number of devices for inputting data to a processing unit, such as a built-in keypad, a data link to another processor, a scanner or a voice data input. A key feature on housing 4 is the aperture 5 through which cable 2 passes. This cable is reel mounted so that it can be retracted entirely within housing 4 or pulled out to its entire length. The extent to which the cable extends from aperture 5 and the angle at which the extended end 6 of the cable takes with respect to the illustrated X-Y-Z coordinate system are detected by the sensor system illustrated in FIGS. 2A–2E.

The sensor arrangement contained in housing 4 and activated by cable 2 contains three sensors similar to those found in a normal computer mouse. Cable 2 passes through a small spherical ball 20 that is in rolling contact with sensors 21, 22 and 23. As the far end 6 of cable 2 is moved to the destination of the lift, the cable direction determines the ball rotation angles which are measured by sensors 22 and 23. Sensor 21 consists of a pair of roller type potentiometers of a well known type that are used to measure the length of cable 2 as it is extended. Sensor 22 also consists of a roller type potentiometer and is used to measure an angle $\alpha$ from the horizontal plane on which the analyzer 1 is resting to the cable 2 as it extends to the origin of the lift. Sensor 23 also consists of a roller type potentiometer that is used to measure the angle B from the vertical X-Z plane in which the analyzer 1 rests when taken from the X axis to the vertical plane containing cable 2 as illustrated in FIG. 1.

Figure 2E:
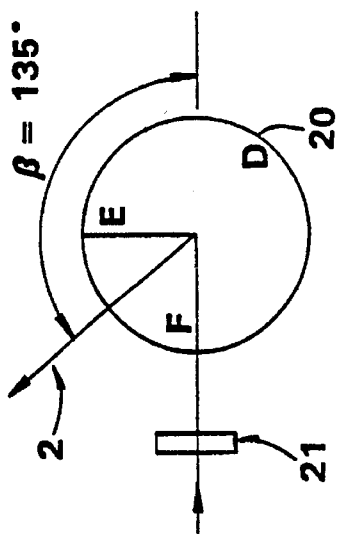
FIGS. 2A–2E illustrate different positions for the sensor array associated with the lift task analyzer.
Figure 2C:
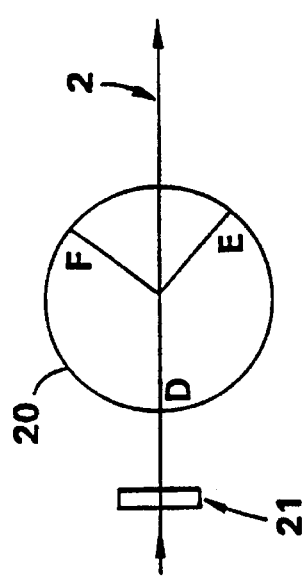
Figure 2D:
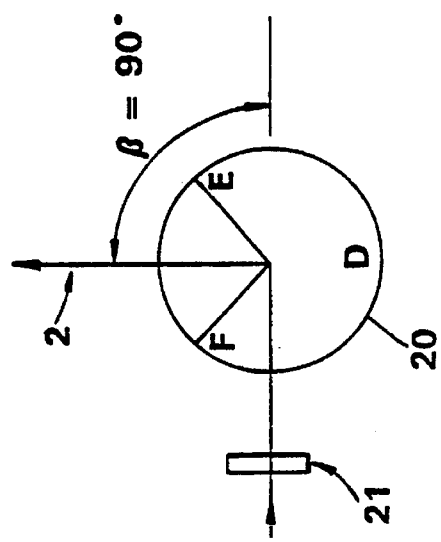
Figure 2A:
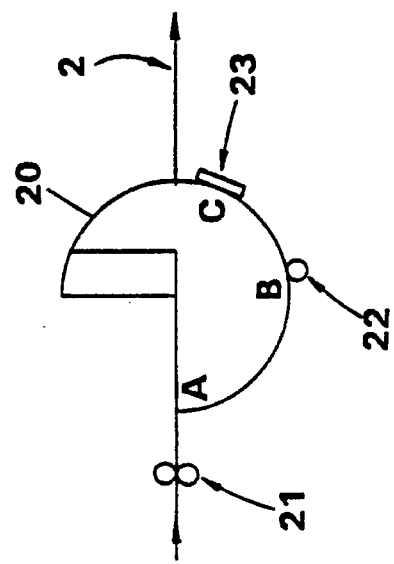
Figure 2B:
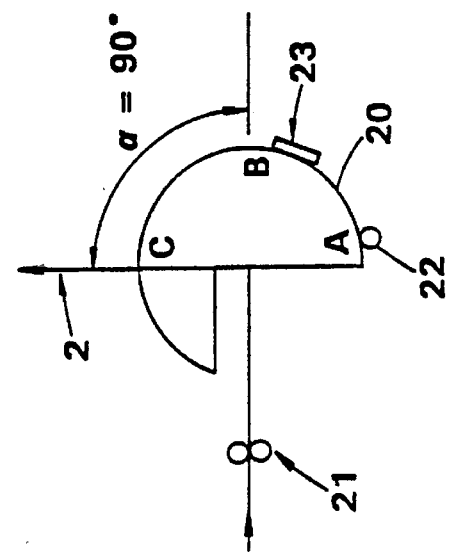

The operation of sensor 22 is illustrated in FIG. 2B. In this figure, roller potentiometer 22 detects the movement of the rotation of spherical ball 20 in the direction shown as a 90° rotation of angle $\alpha$.

As viewed from another angle (top view as opposed to side view) FIGS. 2C–2E illustrate the rotation of spherical ball 20 when rotations indicative of angle $\beta$ are carried out by the movement of the far end 6 of cable 2. Based upon simple trigonometric principles, the outputs of the sensors 21, 22 and 23 can be used to calculate the physical parameters of the lifting task, such as the height above the vertical plane supporting the lift task analysis system 1, the horizontal distance from the origin, vertical displacement and any rotation about the origin (asymmetry angle) necessary to carry out the lifting task. The physical parameters in turn are used to calculate the NIOSH equation multipliers HM, VM, DM, AM based upon predetermined formula as indicated in the Background of the Invention.

Since the determinations of the physical parameters (vertical height and horizontal distance) and certain of the NIOSH equation multipliers are based upon predetermined formulae using the output of sensors 21, 22, 23, such calculations can be carried out by either a microprocessor or a dedicated hard-wired calculation register. Either can be used by the lift task analysis system 1 contained in housing 4. Calculations of the physical parameters can be carried out using values determined at both the origin (where the lifting task starts) and at the destination of the lifting task. The multipliers constituting the recommended weight limit can also be determined for either the origin or the destination of the lifting task or a combination of both.

Figure 3:
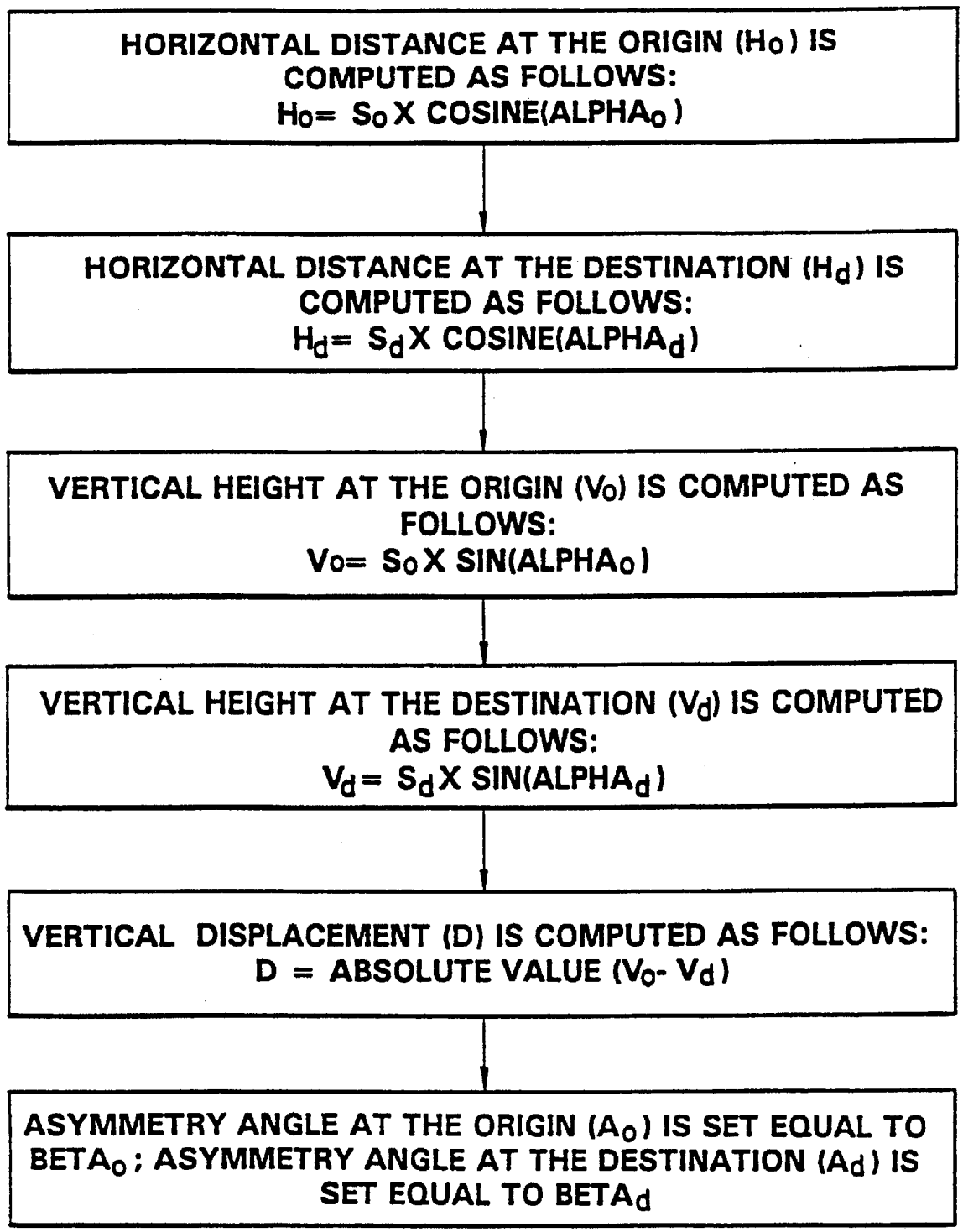
FIG. 3 is an illustration of the calculations used to determine physical parameters based upon the sensor outputs indicative of physical measurements.
Figure 4B:
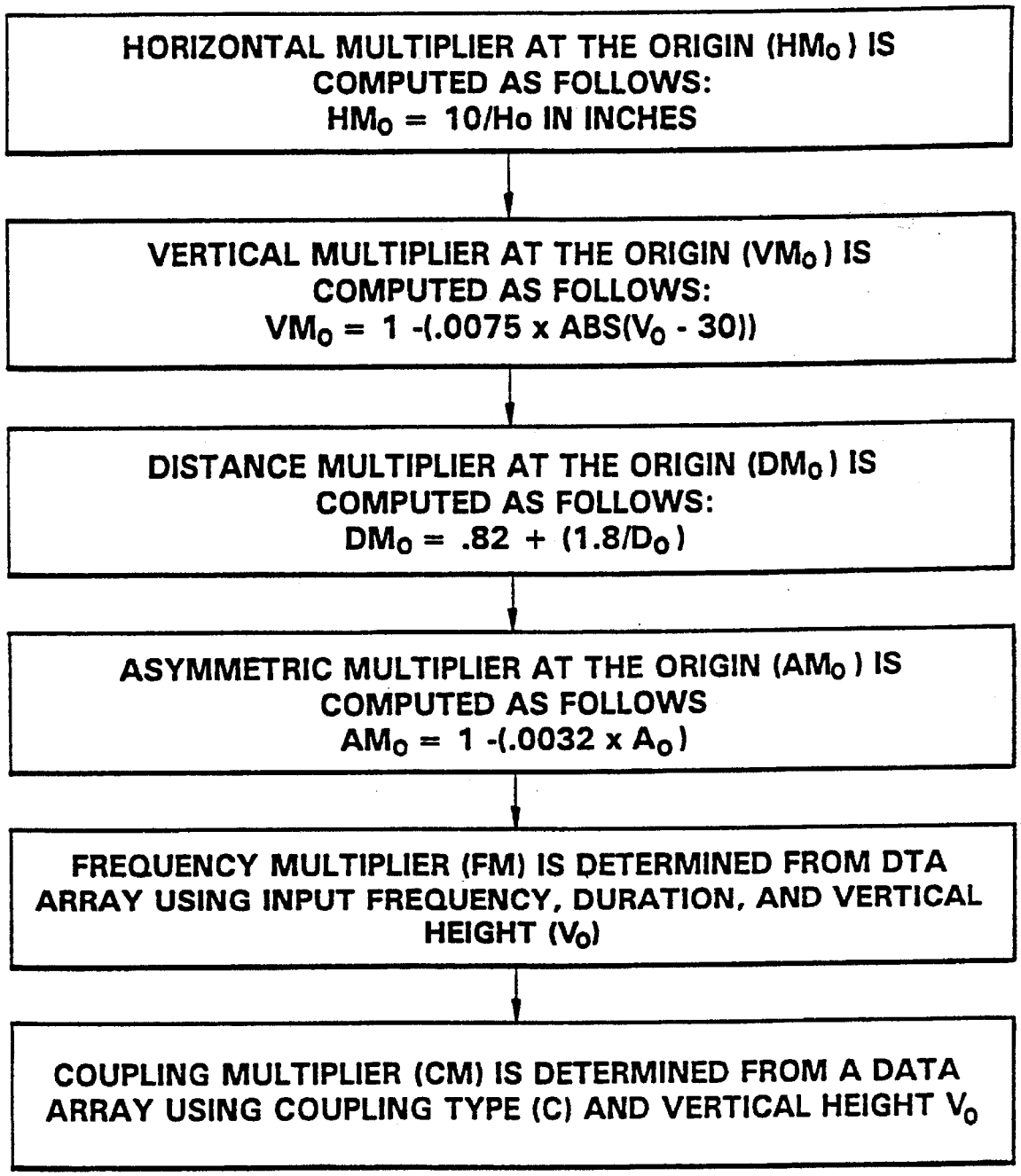
FIG. 4B is a flow chart illustrating the necessary computations to determine four of the six NIOSH equation multipliers for the origin of the lift.

Based upon the measurements of angle $\alpha$, angle $\beta$ and length S (of the extended cable), the horizontal distance, vertical height and overall vertical displacement are calculated. Before such calculations are made, the measured physical parameters can be stored in a memory. Further, a series of such measurements can be stored for a plurality of different lifting tasks before any calculations have been made by the lift task analysis system. Thus, calculations can be easily made for multiple lifting tasks once the physical parameters, horizontal distance, vertical height, angle of asymmetry and overall vertical displacement have been calculated as indicated in FIG. 3, the equation multipliers HM, VM, DM and AM are calculated using the physical parameters as shown in FIG. 4. As with the calculation of physical parameters V, H and D, the calculation of these multipliers can be automatically carried out, or the physical parameters can be stored before the equation multipliers are calculated. Once calculated, the equation multipliers can be stored in a memory or automatically fed to the processor contained in housing 4 to calculate the results of the two NIOSH equations RWL and LI. In the alternative, all the calculations can be carried out by the processor contained in housing 4 which is required for using the two NIOSH equations for recommended weight limit and lifting index.

Figure 5:
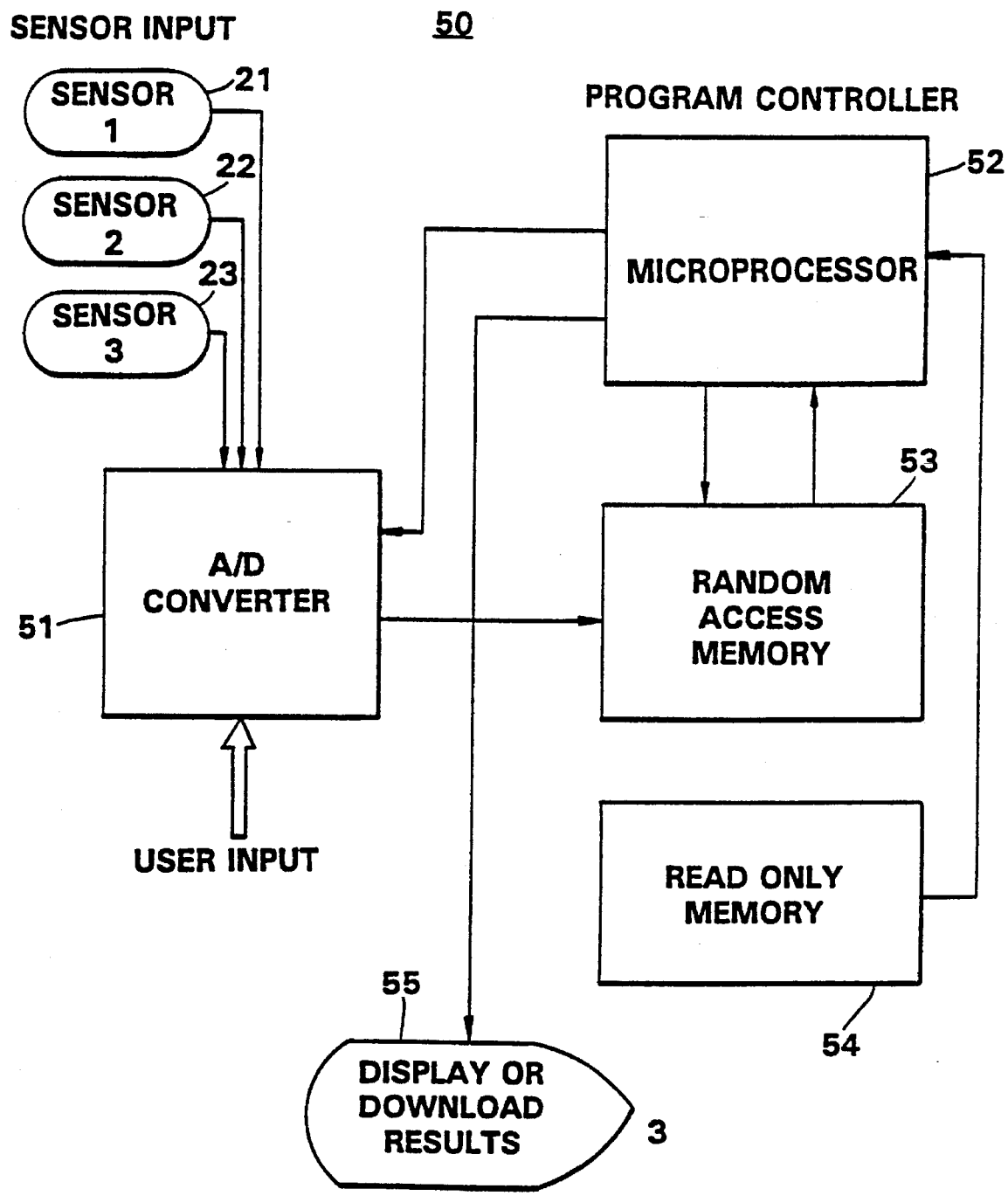
FIG. 5 is a block diagram of the lift task analyzer.
Figure 6B:
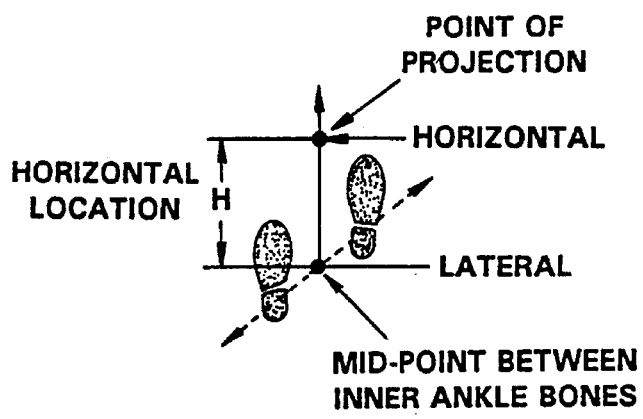
FIG. 6 is an illustration of the coordinates for measuring the horizontal and vertical locations.
Figure 6A:
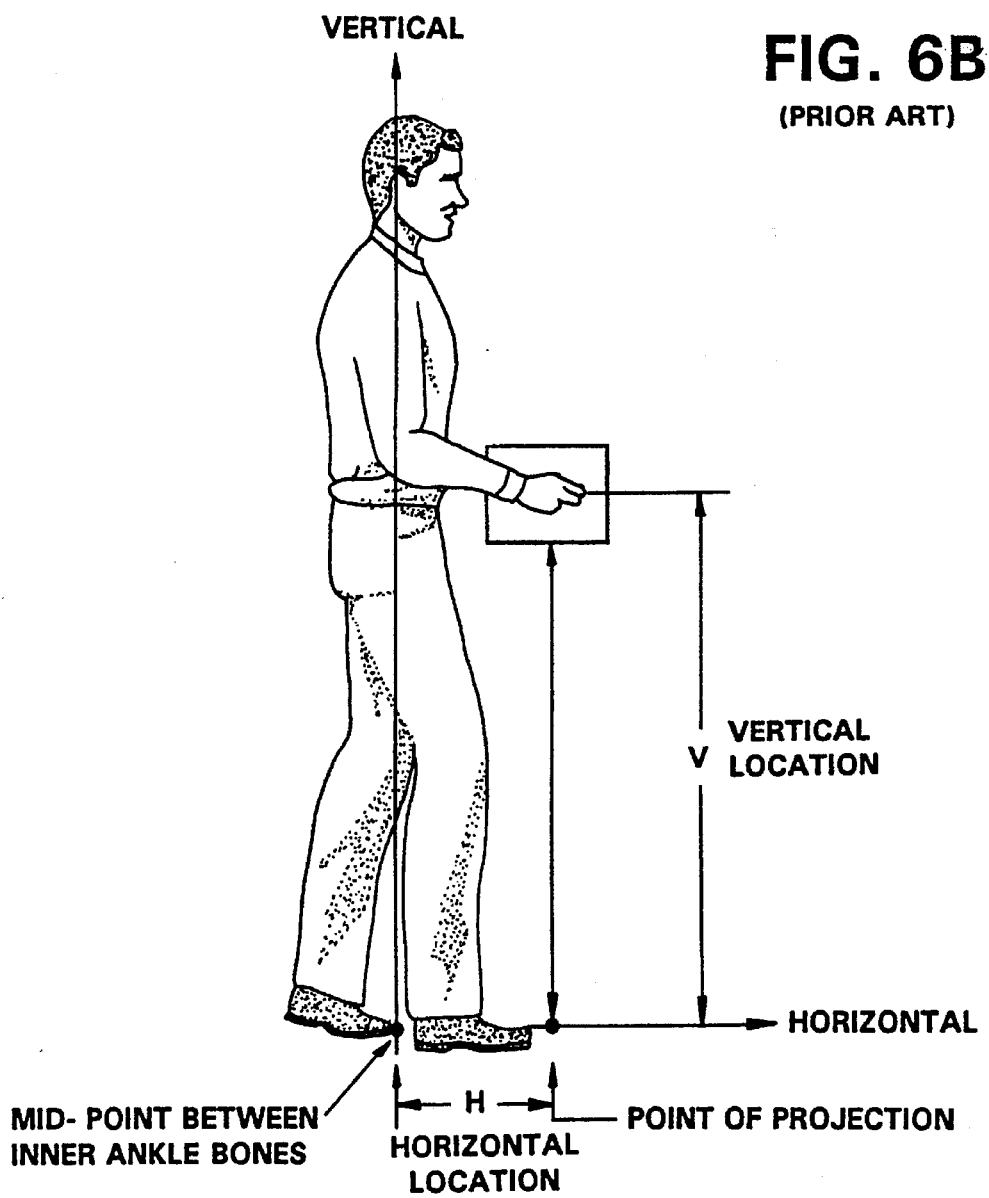
Figure 7B:
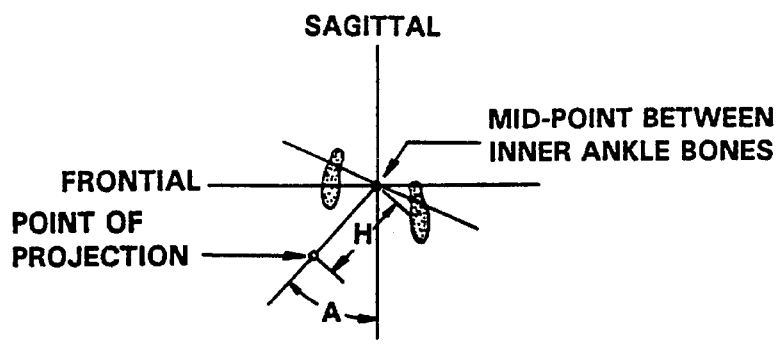
FIG. 7 is an illustration of the coordinates for measuring the angle of symmetry.
Figure 7A:
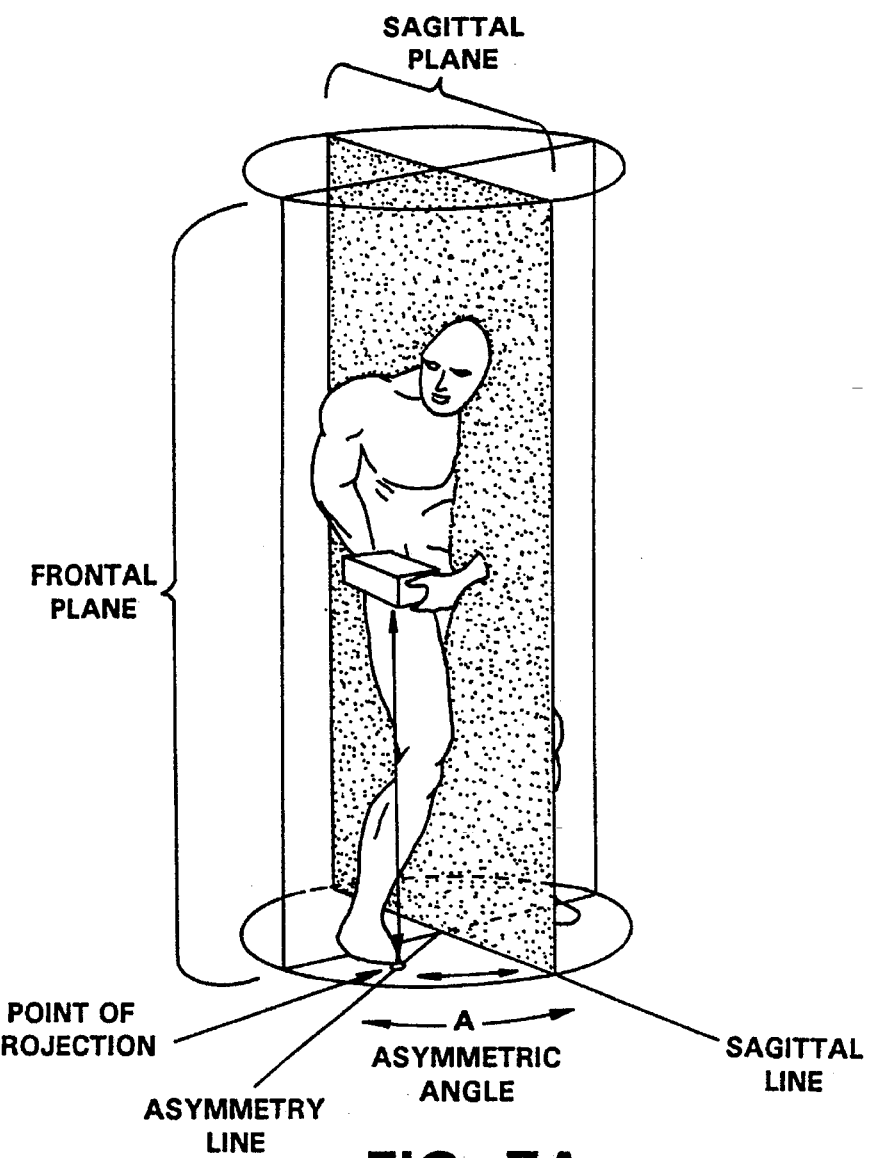

The elements carrying out these functions are illustrated in the block diagram of FIG. 5. As previously stated, sensors 21, 22, 23 operate to provide certain physical parameters associated with the lift task at issue. The outputs of these sensors are fed to an analog to digital converter 51 to place the subject information in condition to be operated upon by the program controller 52. Read only memory 54 is used to store constants associated with all lift task analyses that would be used in any lift task regardless of the other parameters involved. Random access memory 53 is used for the storage of physical measurement values, physical parameters and multipliers once they are calculated.

The recommended weight limit and the lifting index can also be stored in the random access memory once they are calculated. Sufficient memory exists so that multipliers can be stored for a plurality of different lift tasks. In the alternative, both the NIOSH equation multipliers and the results of the NIOSH equations (lifting index and recommended weight limit) can be downloaded through port 55 to an external device or a display 3 (mounted on the casing of the lift task analysis system).

The first equation, recommended weight limit as illustrated on pages 8-9 of this application, requires two multipliers not provided from the calculations based upon the sensor outputs. The first is frequency multiplier (FM), which is determined from a data array derived from Table 1 using frequency, duration and overall vertical height. The second is the coupling multiplier (CM), which is determined from a data array derived from Table 2 using the coupling type and the vertical height. Data on input frequency, duration of the task and coupling type are input by means of a keyboard by the user before the calculations for a specific lifting task are made. The nature of the duration of the lift task and the number of times the task is carried out within a predetermined time period are self-evident. However, coupling type is a far more complex determination and requires the use of tables along with a limited analysis of the size, shape and weight distribution of the object to be lifted, as well as data regarding the individual (such as hand size) carrying out the lift task. A full dissertation for the determination of coupling Waters et al, supra.

Following input of the frequency, duration and coupling data into the lift task analysis system by means of the keyboard, each multiplier is computed, displayed and then stored for future use. Upon a command entered by the keyboard, all the multipliers can be called from memory and used to calculate the recommended weight limit. The solution of this equation will be shown on display 3 and can be placed in memory. The second equation, for lifting index (as illustrated on page 4 of this application) requires the solution to the first equation before the determination of lifting index (LI) can be made.

To calculate LI, the total load weight can be fed into the lift task analysis system via keyboard by the user or can be taken from memory. This value can also be stored and compared with a lifting index for other load weights to determine the maximum weight that can be moved for a particular lifting task (as constituted by the vertical displacement, vertical height, horizontal distance, angular displacement, frequency, duration and coupling type).

The processor, memory, keyboard and display are all well known components which can be easily arranged and programmed to carry out the necessary calculations and storage of the results of those calculations. Consequently, there is no reason to further elaborate on the nature of any of these elements. Rather, it is the use of the sensor arrangement shown in FIGS. 2A–2E creating an automatic input for the calculation of the physical parameters used to calculate the NIOSH equation multipliers HM, VM, DM and AM which is unknown in the field of environmental health and safety control. Further, the lift task analysis system can be arranged to provide automatic calculation of the subject NIOSH equation multipliers for storage or automatic use in the NIOSH equations. It is the combination of a particular type of sensor and calculating means dedicated to a particular equation set which provides the benefits of quick and easy use, thereby facilitating efficient analysis of each lift task so as to avoid worker injury.

As will be appreciated by persons of ordinary skill in the art from an understanding of the above-detailed description, the three-dimensional position of the mid-point of the hands can be used to determine the factors needed to calculate the NIOSH recommended weight limit and lifting index for a specified lifting task. No actual weight is lifted by the participant and only the physical locations of his or her hands is important. The weight of the object to be lifted in counterpart real-life lifting activity is then entered into the calculation, along with lifting frequency, duration, and the rating of the coupling quality as explained above.

Although a number of arrangements of the present invention have been mentioned by way of example, it is not intended that the invention be limited thereto. For example, the present invention can be adapted for use with a direct (hard-wired) connection to a PC or can be provided with a radio link to a central control unit for correlation of large numbers of lift task analyses, comparisons and recommendations. Accordingly, this invention should be considered to include any and all configurations, modifications, variations, combinations or equivalent arrangements falling within the scope of the following claims.

I claim:

1. A lift task analysis system arranged to analyze specific lifting tasks, comprising:

(a) motion parameters measuring means, comprising a length of cable retractably stored and having a distal end movable by the hands of a person relative to an origin in a three-dimensional polar coordinate reference frame in correspondence with three-dimensional movements made by the person during a selected lifting task, means for determining physical locations of the distal end of the cable held by the person's hands and generating corresponding outputs in terms of three spherical polar coordinates relative to the origin, a horizontal plane containing the origin and a vertical plane containing the origin;

(b) input means for enabling a user to input selected parameters;

(c) a control processor including
  (i) means for determining a recommended weight limit for the selected lifting task based upon said outputs from said physical location determining means and said user-inputted parameters;
  (ii) means for determining a lifting index for the selected lifting task based upon said recommended weight limit and the user-inputted parameters; and (d) memory means for storing said lifting index and said recommended weight limit.

2. The lift task analysis system of claim 1, further comprising:
means for displaying the contents of said memory means.

3. The lift task analysis system of claim 1, wherein:
said means for determining physical locations comprises three pairs of roller-type potentiometers, a first pair of said potentiometers being dedicated to determining a cable length extended relative to said origin, a second pair of said potentiometers being dedicated to determining a first angle in said spherical polar coordinates, and a third pair of said roller-type potentiometers being dedicated to determining a second angle in said spherical polar coordinates.

4. The lift task analysis system of claim 1, wherein:
said user-inputted parameters comprise frequency of lifting, duration of lifting, coupling type, and load weight.

5. The lift task analysis system of claim 1, wherein:
said means for determining said recommended weight limit determines a first recommended weight limit at an origin point and a second recommended weight limit at a destination point.

6. The lift task analysis system of claim 1, wherein:
said means for determining said lifting index determines a first lifting index at an origin point and a second lifting index at a destination point.

7. The lift task analysis system of claim 6, wherein:
said control processor further comprises means for determining a first horizontal distance at said origin point, a second horizontal distance at a destination point, a first vertical height at said origin point, a second vertical height at said destination point, a vertical displacement corresponding to said first and second vertical heights, a first asymmetry angle at said origin point, and a second asymmetry angle at said destination point.

8. The lift task analysis system of claim 7, wherein:
said means for determining said recommended weight limit comprises means for determining a horizontal multiplier ($HM_O$) at said origin point, a horizontal multiplier ($HM_D$) at said destination point, a vertical multiplier ($VM_O$) at said origin point, a vertical multiplier ($VM_D$) at said designation point, a distance multiplier ($DM_O$) at the original point, a distance multiplier ($DM_D$) at the destination point, an asymmetric multiplier ($AM_O$) at the origin point, an asymmetric multiplier ($AM_D$) at the destination point, a frequency multiplier (FM), and a coupling multiplier (CM).

9. The lift task analysis system of claim 8, wherein:
said recommended weight limit at the origin ($RWL_O$) is defined by the equation $$RWL_O = 51 \times HM_O \times VM_O \times DM_O \times AM_O \times FM \times CM,$$

and said recommended weight limit at the destination ($RWL_D$) is defined by the equation $$RWL_D = 51 \times HM_D \times FM_D \times DM_D \times AM_D \times FM \times CM.$$

10. The lift task analysis system of claim 9, wherein:
said lifting index at the origin ($LI_O$) is defined as $L/RWL_O$, where L is a weight of a load lifted by the user in correspondence with the distal end of the cable,
and said lifting index at the destination ($LI_D$) is defined as $L/RWL_D$, where L is the weight of the load.

11. The lift task analysis system of claim 10, wherein:
said first horizontal distance ($H_O$) is defined as $H_O = S_O \times \cos \alpha_O$, where $S_O$ is the length of the cable at said origin point and $\alpha_O$ is a first angle at said origin point;
said second horizontal distance ($H_D$) is defined as $H_D = S_D \times \cos \alpha_D$, where $S_D$ is the length of the cable and the destination point at $\alpha_D$ is a first angle at said destination point;
said first vertical height ($V_O$) is defined as $V_O = S_O \times \sin \alpha_D$;
said second vertical height ($V_D$) is defined as $V_D = S_D \times \sin \alpha_D$;
said vertical displacement (D) is defined as $D = |V_O - V_D|$;
said first asymmetry angle ($A_O$) is set equal to ($\beta_O$), where $\beta_O$ is the second angle at said origin point;
and, said second asymmetry angle ($A_D$) is set equal to $\beta_D$, where $\beta_D$ is the second angle at the destination.

12. The lift task analysis system of claim 8, wherein:
$HM_O = 10/H_O$ (in inches);
$VM_O = 1 - (0.0075 \times |V_O - 30|)$;
$DM_O = 0.82 + (1.8/D_O)$; and
$AM_O = 1 - (0.0032 \times A_O)$.

13. The lift task analysis system of claim 12, wherein:
FM is determined from a data array comprising frequency, duration and $V_O$; and
CM is determined from a data array comprising coupling type and $V_O$.

14. The lift task analysis system of claim 8, wherein:
$HM_D = 10/H_D$ (in inches);
$VM_D = 1 - (0.0075 \times |V_D - 30|)$;
$DM_D = 0.82 + (1.8/D_D)$; and
$AM_{Dd} = 1 - (0.0032 \times A_D)$.

15. The lift task analysis system of claim 14, wherein:
$FM_D$ is determined from a data array comprising frequency, duration and VD; and
$CM_D$ is determined from a data array comprising coupling type and $V_D$.

16. The lift task analysis system of claim 1, further comprising:
means for printing said lifting index and said recommended weight limit.

17. The lift task analysis system of claim 1, wherein:
a first recommended weight limit and a first lifting index are determined at an origin point, and a second recommended weight limit and a second lifting index are computed at a destination point.

18. The lift task analysis system of claim 17, wherein:
a composite recommended weight limit and a composite lifting index are determined based upon the first and second recommended weight limits, and the lifting index at the origin and the lifting index at the destination, respectively.

19. A method of analyzing specific lifting tasks performed by a user, comprising the steps of:
- (a) providing a retractably stored and user-extendable length of cable having a distal end held in the hands of the user and movable by the user to a location determinable relative to an origin in three-dimensional space in a polar coordinate reference system during a selected lifting task;
- (b) determining physical locations of the distal end during the selected lifting tack and generating corresponding outputs in terms of three spherical polar coordinates, a length of cable extended relative to the origin, a first angle measured relative to a first line in a horizontal plane containing the origin and a second angle measured relative to a second line in a vertical plane containing the origin;
- (c) operating an input means to input user-selected parameters to a means for storing and processing data;
- (d) determining a recommended weight limit for the selected lifting task based upon said outputs from said physical location determining means and said user-inputted parameters;
- (e) determining a lifting index for the selected lifting task based upon said recommended weight limit and the user-inputted parameters; and
- (f) storing said lifting index and said recommended weight limit for user reference in a memory of the data processing means.

20. The method according to claim 19, comprising the further step of:
- (g) displaying the contents of said memory.

* * * * *